United States Patent [19]

Kozam et al.

[11] 4,367,737
[45] Jan. 11, 1983

[54] MULTIPLE BARREL SYRINGE

[76] Inventors: George Kozam, 234 E. Clinton Ave., Tenafly, N.J. 07670; Pat Romanelli, 224 Brook St., Harrington Park, N.J. 07640

[21] Appl. No.: 251,311

[22] Filed: Apr. 6, 1981

[51] Int. Cl.³ .............................................. A61M 5/00
[52] U.S. Cl. ............................. 128/215; 128/218 NV
[58] Field of Search ................... 128/215, 216, 218 R, 128/218 P, 218 M, 234, 224, 214 R, 218 NV; 222/137, 136, 135, 143, 145, 386

[56] References Cited

U.S. PATENT DOCUMENTS

| | | | |
|---|---|---|---|
| 1,948,388 | 2/1934 | Liberson | 128/234 |
| 3,747,812 | 7/1973 | Karman et al. | 128/215 X |
| 4,044,757 | 8/1977 | McWhorter et al. | 128/234 |
| 4,109,653 | 8/1978 | Kozam et al. | 128/218 R |
| 4,195,631 | 4/1980 | Baucom | 128/214 R |

Primary Examiner—John D. Yasko
Attorney, Agent, or Firm—Edward F. Levy

[57] ABSTRACT

A multiple barrel syringe for selective delivery of fluids which comprises a body having a pair of bores each containing a plunger and each terminating in a smaller sized conduit for receiving fluid from the bores. Connected to the body is a movable member having a single conduit or passage and a needle mounted on the member and communicating with the bore. The movable member may be manually actuated to bring its single conduit into communication with a selected bore conduit for providing passage of fluid from the selected bore to the needle. The movable member may then be moved to another position to bring the needle into communication with the other bore. Sealing means are provided on the movable member to avoid leakage and feedback of fluid from or to the bore not dispensing fluid.

10 Claims, 10 Drawing Figures

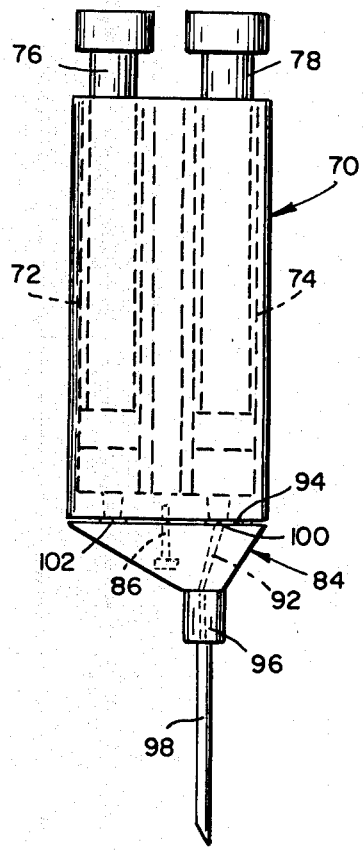
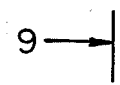
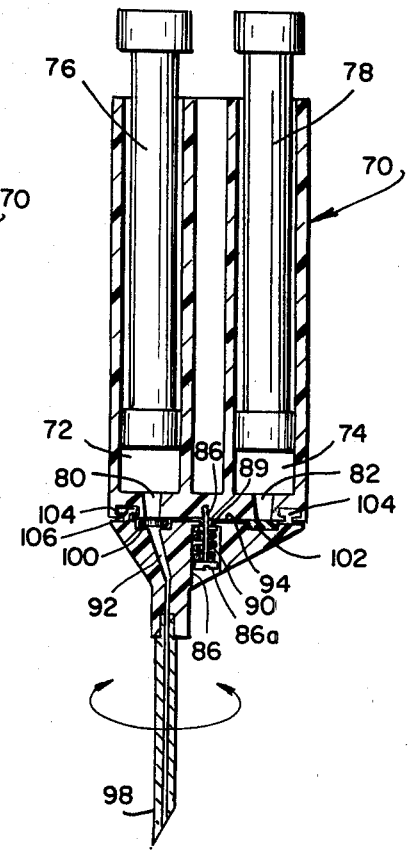
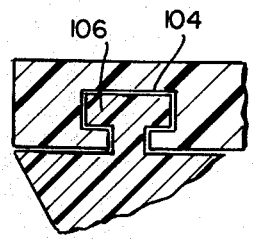

MULTIPLE BARREL SYRINGE

The present invention relates to hypodermic syringes of the type used in the medical field, and in particular to a multiple barrel syringe for the successive dispensing of different fluids in a pre-arranged selected manner.

In our U.S. Pat. No. 4,109,653, filed Aug. 29, 1978, and entitled "Multiple Barrel Syringe", we have disclosed a successive delivery multiple syringe which comprises a body formed with a pair of bores, each containing a different fluid to be dispensed, each of said bores containing a slidable plunger. The syringe mounts a single needle through which the fluid is dispensed, and each bore communicates with the needle through a respective one-way valve in the nature of a rubber duck-bill valve. Depression of either of the plungers produces fluid pressure in the associated bore which opens up its one-way valve to enable the fluid from said bore to pass through the needle. Mixing of the fluids within the syringe from one bore to the other is eliminated or made negligable by the inclusion of the one-way valves and by the provision of small conduits which lead from the one-way valve to the needle.

The syringe shown in U.S. Pat. No. 4,109,653 is particularly adapted for use in dental root canal therapy in which debrided particles are removed by first injecting hydrogen peroxide under pressure into the root canal, and immediately thereafter injecting a chlorinated soda solution such as sodium hypochlorite into the root canal. Since two syringes are normally required for this successive injection, the use of a single syringe having two barrels containing the different fluids was found beneficial and effective in decreasing the time between successive injections and reducing the number of syringes used with a consequent saving of time of loading and sterilization.

In the aforementioned multiple barrel syringe, two one-way valves were required to prevent fluid from one barrel from entering the other barrel during operation, which would result in premature mixing of the fluids. The valves increased the cost of the syringe in manufacture and also required individual cleaning and maintenance to prevent clogging and malfunctioning.

The invention as contemplated herein completely avoids the use of valves as taught by our previous patent, and provides instead a direct flow of the fluid from the syringe bore to the needle via conduit paths each of which is selectively blocked depending upon the fluid desired.

Accordingly one embodiment of the invention provides a selective delivery multiple barrel syringe having a body portion containing a pair of bores, with each bore containing a plunger. Each bore terminates in a recess and conduit for the free flow of fluid outwardly from the bore. Pivotally attached to the body at its lower extremity is a pivotally movable member having a single needle disposed to align with a particular conduit for the receiving of fluid in accordance with the selected pivoted action of the movable member, the other conduit being blocked to avoid fluid feedback.

Another embodiment of the invention is comparable to the first and has mounted on the body a swivel-like rotatable member for selected positioning of the conduits and the needle. Here again the needle is aligned with the transmitting bore and conduit, the other bore conduit being blocked.

It is therefore a principle object of the invention to provide a selective and/or successive delivery multiple barrel syringe free of any control valves for the discharge of two or more solutions required through a single hypodermic needle, and to allow for loading of the syringe barrels through the needle.

Another object of the invention is to provide a selective delivery multiple barrel syringe having fewer parts, and being less expensive, easier to clean, sterilize and maintain.

Still another object of the invention is to provide a selective delivery multiple barrel syringe which effectively avoids the interaction of solutions between bores during the dispensing of a selected solution.

Other objects and advantages of the invention will become apparent during the course of the following specification when taken in connection with the accompanying drawings, in which:

FIG. 7 is a front elevational view of a selective delivery multiple barrel syringe in accordance with another embodiment of the invention;

FIG. 8 is a side view of FIG. 7;

FIG. 9 is a sectional view taken along the line 9—9 of FIG. 8; and

FIG. 10 is an enlarged detailed view of a "T" slot and rivet support shown in FIG. 9.

Figure 1:
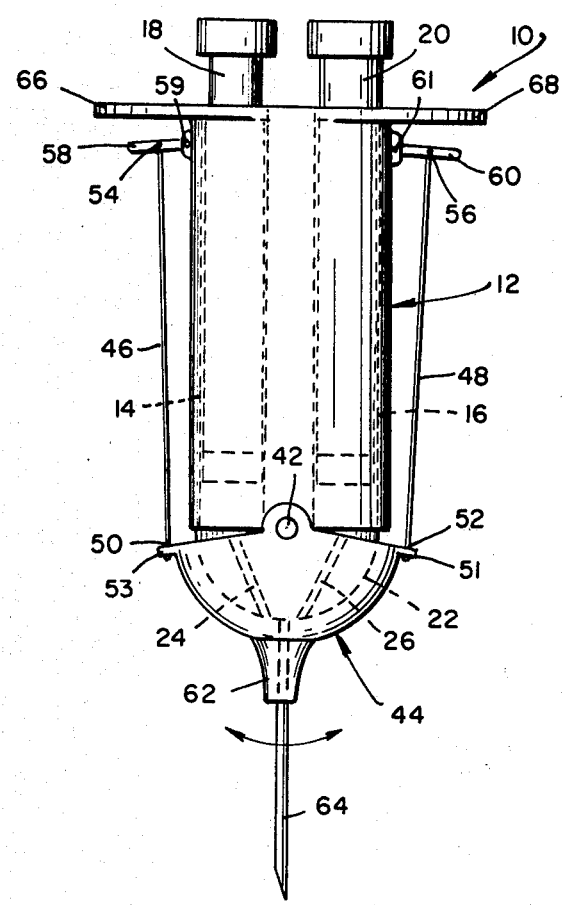
FIG. 1 is a front elevational view of a selective delivery multiple barrel syringe in accordance with the present invention.
Figure 2:
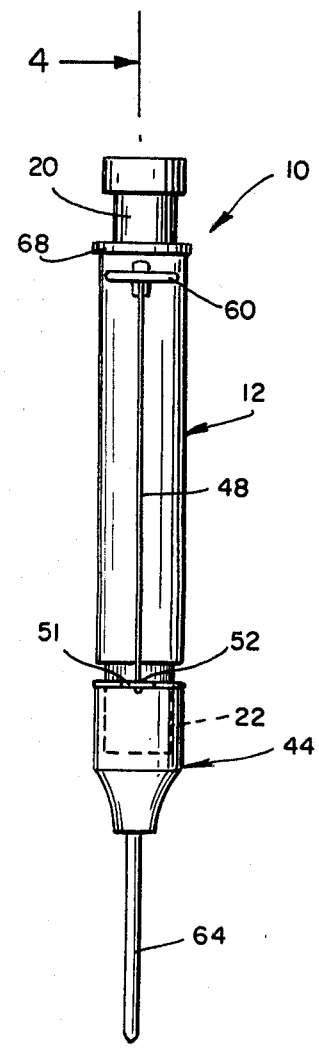
FIG. 2 is a side view of FIG. 1.
Figure 3:
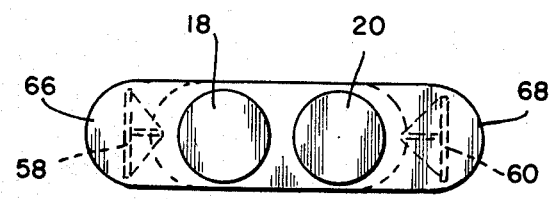
FIG. 3 is a top plan view of FIG. 1.

Referring in detail to the drawings and in particular to FIGS. 1, 2 and 3, there is shown a successive delivery multiple barrel syringe 10 made in accordance with the present invention and comprising a body 12 having a pair of separated parallel bores 14, 16 each of which contains a plunger 18, 20.

Figure 4:
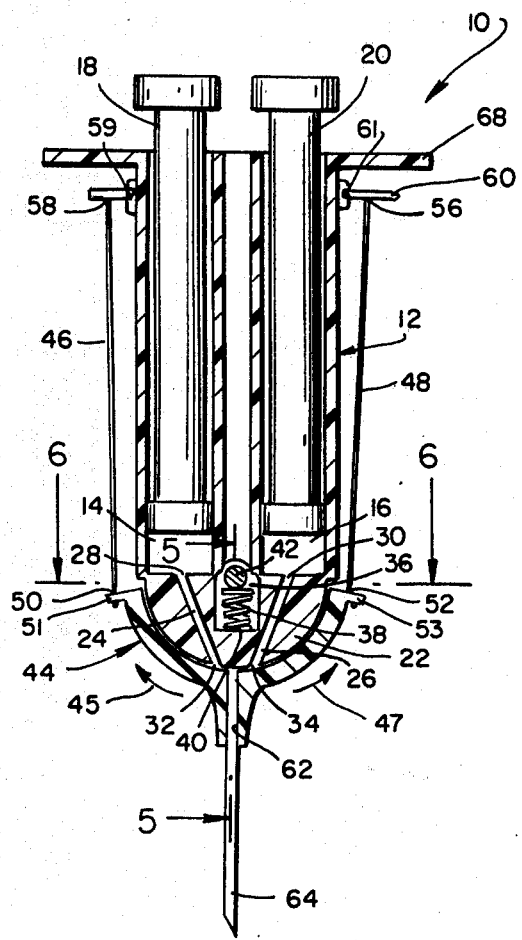
FIG. 4 is a sectional view taken along the line 4—4 of FIG. 2.
Figure 5:
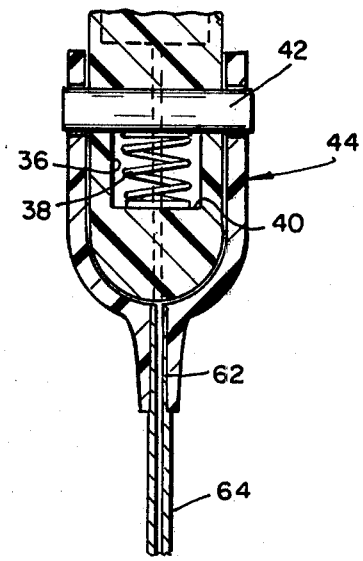
FIG. 5 is an enlarged fragmented view taken along the line 5—5 of FIG. 4.
Figure 6:
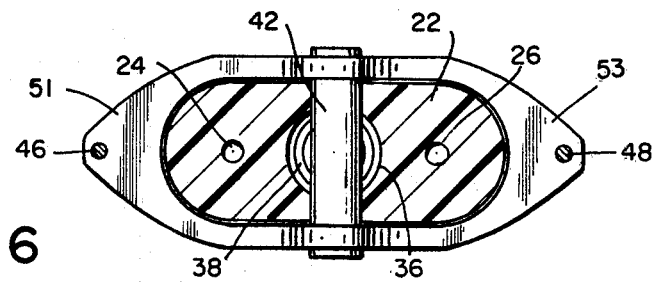
FIG. 6 is an enlarged sectional view taken along the line 6—6 of FIG. 4.

FIGS. 4, 5 and 6 show in more detail the syringe body 12 terminating at its lower extremity in a fixed semi-circular solid end portion 22 formed with a pair of angularly-extending through bores or conduits 24 and 26 which converge from top to bottom. At their upper ends, the conduits 24 and 26 have respective inlet orifices 28 and 30, and at their opposite ends respective outlet orifices 32 and 34. Conduit 24 communicates with bore 14 through orifice 28 for receipt of fluid therefrom, while conduit 26 communicates with bore 16 through orifice 30.

The fixed end portion 22 is further provided with a cylindrical recess or well 36 for receiving a compression coil spring 38 which compressively bears against the surface 40 of the recess, and a transverse pivot pin 42 to be described.

Mounted on the end portion 22 is a needle carrier member 44 in the form of a hollow, shell like member having an interior cavity shaped to conform to the exterior surface of the end portion 22 and fitting closely thereon. The member 44 is pivotally mounted on the body 10 by the transverse pivot pin 42 in such a manner that the inner surface of the member 44 makes slidable frictional contact with the outer surface of the end portion 22, and the member 22 is pivotally movable upon the syringe body 10 in the clockwise and counter-clockwise directions indicated by the arrows 45 and 47 in FIG. 4.

Actuation of the needle carrier member 44 in its pivotal movement is accomplished by a pair of rods 46, 48 each connected at one of their extremeties 50,52 to opposite sides of said member 44 along a pair of outwardly extending flanges 51,53 projecting outwardly from the periphery of said shell 44. The other rod extremeties 54, 56 are respectively connected to activating levers 58, 60, which are pivotally mounted on body 12 by pivots 59, 61. Further, the shell member 44 is always held in pressure-contact with the fixed end portion 22, along their abutting surfaces, through the facility of the coil spring 38 exerting outward pressure upon the pivot 42 supporting the shell member 44 and on the fixed end portion 22, thus preventing fluid leakage between the abutting surfaces.

The needle carrier member 44 is formed with an extended needle bore 62 at the apex or dome area of the shell for receiving a syringe needle 64 retained therein in the usual manner for the receiving and dispensing of fluids. The selective movement of the shell needle carrier member 44 causes the bore 62 and needle 64 to align and communicate alternately with the outlet orifices 32, 34 of the respective conduits 24, 26 and thus communicate with the bores 14, 16. When the respective bore 14 conduit 24 and needle bore 62 are in alignment and communication for the dispensing of fluid, the conduit 26 is non-functional and is blocked by the shell member abutting surface, from receiving or transferring fluid. Similarly conduit 24 is blocked when bore 16, conduit 26 and needle bore 62 are aligned and in communication.

The syringe body 12 includes integrally formed finger grips 66 and 68 which project outwardly from the upper end of said body and which facilitate holding the syringe tightly during use. The activating levers 58 and 60 are mounted directly beneath the respective finger grips 66 and 68, and, as previously described, the selective movement of the needle carrier member 44 is effected by manipulation of levers 58, 60. The levers are normally horizontally positioned, as shown in FIG. 4, thereby locating the needle carrier member 44 in a neutral, inoperative position with needle bore 62 located midway between and out of communication with the outlet orifices 32 and 34 of conduits 24 and 26. In this neutral position, no fluid will be dispensed from either bore 14 or 16 to the needle 64 even if downward pressure is applied to one of the plungers 18 or 20.

When the syringe 10 is to be used to dispense fluid, the operator holds the syringe in the usual manner with his thumb overlying one of the plungers and his fingers underlying the finger grips 66 and 68. The user now ascertains which of the bores 14 or 16 is to dispense its fluid first, and moves his finger to underlie the lever 58 or 60 located adjacent to the selected bore. For example, if the treatment procedure requires that fluid first be dispensed from bore 14, the user would move his finger to underlie the lever 58 adjacent bore 14. Movement of the thumb and fingers toward each other effects downward pressure on the plunger 18 and at the same time pivot the lever 58 in an upward direction, thereby raising rod 46 and causing needle carrier member 44 to turn in a clockwise direction until the needle bore 62 and needle 64 come into registry with the outlet orifice 32 of fluid conduit 24. Simultaneous depression of plunger 18 thus causes fluid to flow from bore 14 through conduit 24 and through the registering needle 64. Subsequently, when a different fluid is to be dispensed from bore 16, the user need merely adjust his grip on the syringe so that his finger underlies the other activating lever 60 and his thumb presses upon the plunger 20. Hand pressure will then pivot lever 60 upwardly, raising rod 48 and thereby causing needle carrier member 44 to turn in a counter-clockwise direction until the needle bore 62 and needle 64 come into registry with the outlet orifice 34. Liquid is thus fed from the bore 16 to the needle 64.

The levers 58 and 60 are made of such a length and are so positioned that the raising of either lever to its fullest extent will cause the needle carrier member 44 to turn through the exact distance necessary to bring the needle bore into precise registry with the respective outlet orifice 32 or 34. As shown in FIG. 5, the pivot pin 42 is mounted in an elongated slot so that upward pressure thereon by compression spring 38 provides an effective seal between the confronting surfaces of needle carrier member 44 and end portion 22, and also maintains the needle carrier member in either of its tilted positions.

It will be seen that whenever the needle bore 62 and needle 64 are in registry with one of the fluid conduits, the outlet orifice of the other fluid conduit is sealed off by the underlying body of the needle carrier member 44. This prevents fluid from one bore from entering into the other bore or mixing with fluid from the latter during operation of the syringe and is accomplished without the use of valves.

Referring now to FIGS. 7,8 and 9, there is shown another embodiment of multiple barrel syringe made in accordance with the present invention. The syringe body 70 is formed with two spaced fluid retaining bores 72 and 74, which contain respective plungers 76 and 78. The bores 72 and 74 terminate at their lower ends in respective downwardly tapered fluid conduits or bores 80 and 82 for receiving fluid therefrom. The bores 72 and 74 open through the bottom surface of body 70.

Rotatably mounted on the bottom end of the syringe body 70 is a needle carrier member 84 having an upper body portion 84a, the top surface 94 of which conforms in size and shape to the bottom surface of syringe body 70. The body portion 84a tapers downwardly to a needle mounting portion 96 which is off-center of the upper body portion 84a. The needle carrier member 84 is rotatably mounted on the body 70 by means of a spring-loaded screw 86 located within a central cavity 88 in the needle carrier member and serving as an axis for rotation of the needle carrier member on the syringe body 70. The screw 86 is threadedly secured to the center of the syringe body 70 and depends therefrom into a central circular cavity 88 in the needle carrier member 84. The cavity 88 is bordered at its upper end by an overhanging annular ledge 89, and a coiled compression spring 90 surrounds the screw shank with its upper end seated against the bottom surface of the ledge 89 and its other end seated against the enlarged head 86a of screw 86. The compression spring 90 exerts downward biasing pressure upon the screw head 86a and therefore urges the syringe body 70 into firm engagement with the needle carrier member 84. The screw shank fits closely through the central aperture of annular ledge 89, and the enlarged screw head fits snugly within the cavity 88 so that the needle carrier member 84 is guided for rotation about screw 86.

As shown in FIG. 9, the needle carrier member 84 is further provided with an off-center, downwardly-tapered bore 92 which extends downwardly from the top body-abutting surface 94 to the needle mounting portion 96 within which it communicates with hollow needle 98 mounted therein and having the usual passage for the transmission of fluids.

The off-centered needle bore 92 is so positioned that it will move selectively into communication with either of the outlet bores 80 or 82 when the needle carrier member 84 is turned to either of two operative positions. In the first operative position, shown in FIG. 9, the needle bore 92 is in communication with the outlet bore 80 which communicates with the syringe fluid retaining bore 72. The needle carrier member 84 may then be turned about pin 86 through an angle of 180° to the second operative position of FIG. 7, in which the needle bore 92 is in communication with the outlet bore 82 leading from the other fluid retaining bore 74. When the needle carrier member 84 is in its first operative position of FIG. 9 and the plunger 76 is depressed, fluid is forced from bore 72 through needle bore 92 to the needle 98. When the needle carrier member 84 is manually turned to its second operative position of FIG. 7 and the plunger 78 is depressed, fluid is forced from bore 74 through needle bore 92 to needle 98. Leakage of fluid from between the rotatable member 84 and the syringe body 70, during use, is prevented by the mounting of a resilient O-ring 100 in a depression surrounding the needle bore 92 to provide a seal thereabout, and by a diametrically-opposed flat resilient disc 102 embedded in the upper surface of needle carrier member 84 and positioned to underlie and seal off the non-functioning outlet bore 80 or 82.

It is necessary and desirable to insure that, in either operative position of the needle carrier member 84, the needle bore 92 is in exact registry with the outlet bore 80 in its first operative position, and is in exact registry with the outlet bore 82 in its second operative position. To accomplish such precise registry the syringe body 70 is formed with an elongated slot 104 of T-shaped cross section which extends arcuately from one side of the body 70 to the other at the lower end thereof. FIG. 9 shows the two ends of the T-slot 104, one end being in alignment with and adjacent to the outlet bore 80, and the other end being in alignment with and adjacent to the outlet bore 82. Mounted on the needle carrier member 84 is a T-shaped rivet 106 which fits slidably within the slot 104 and slides from one end of the slot to the other end when the needle carrier member is turned between its two operative positions. The rivet 106 is so located that when the needle carrier member 84 is turned to its first operative position, the rivet engages one end of the T-slot 104 which acts as a stop to position the needle bore 92 in accurate registry with the outlet bore 80, and when the needle carrier member is turned to its second operative position, the rivet 106 engages the other end of the T-slot 104, which acts as a stop to position the needle bore 92 in accurate registry with outlet bore 82.

While preferred embodiments of the invention have been shown and described herein, it is obvious that numerous omissions, changes and additions may be made therein without departing from the spirit and scope of the invention.

What is claimed is:

1. A multiple barrel syringe for the selective dispensing of fluids, comprising
   a body portion having a pair of independent fluid-retaining bores, a pair of individually depressible plungers extending respectively into said bores, and a first fluid conduit and second fluid conduit communicating with the respective bores and opening through the bottom surface of said body portion at spaced locations thereon,
   a needle carrier member mounted on said body portion below the bottom surface thereof and comprising an upper body portion, a depending portion mounting a hollow needle, and a single needle bore extending through said upper body portion and communicating with said hollow needle,
   and means movably mounting said needle carrier member on said syringe body portion for movement of said needle carrier member between a first operative position in which said needle bore is in registry with and communicates with said first fluid conduit and said second fluid conduit is covered over and blocked by the upper body portion of said needle carrier member, and a second operative position in which said needle bore is in registry with and communicates with said second fluid conduit and said first fluid conduit is covered over and blocked by the upper body portion of said needle carrier member.

2. A multiple barrel syringe according to claim 1 in which said needle bore communicates with the fluid conduit of a first of said pair of bores in the first operative position of said needle carrier member, whereby depression of the plunger of said first bore will discharge fluid from the latter through its communicating fluid conduit and said needle bore to said hollow needle, and in which said needle bore communicates with the fluid conduit of the second of said pair of bores in the second operative position of said needle carrier member, whereby depression of the plunger of said second bore will discharge fluid from the latter through its communicating fluid conduit and said needle bore to said hollow needle, said syringe also including means for urging the upper body portion of said needle carrier member into firm engagement with said syringe body portion, whereby to prevent leakage between said two fluid conduits.

3. A multiple barrel syringe according to claim 2 in which said syringe body portion has an arcuate bottom surface and said needle carrier member has a shell-like upper body portion having a concavity fitting closely and slidably against said arcuate bottom surface, and in which said mounting means comprises a pivot pin pivotally mounting the shell-like upper body portion of said needle carrier member on said syringe body portion.

4. A multiple barrel syringe according to claim 3 in which said pivot pin extends transversely through said syringe body portion and through the needle carrier member, and in which a compression spring is mounted in said syringe body portion and bears against said pivot pin in a direction to urge the arcuate bottom surface of said syringe body portion and the concavity of said needle carrier member into firm abutting engagement with each other, whereby to prevent leakage between said fluid conduits.

5. A multiple barrel syringe according to claim 3 which includes actuating means for selectively moving said needle carrier member between its first and second operative positions, said actuating means comprising a pair of spaced levers pivotally mounted on opposite sides of said syringe body portion at the upper end thereof, and a pair of elongated coupling members connecting the respective levers to opposite sides of said needle member.

6. A multiple barrel syringe according to claim 2 in which said syringe body portion has a flat bottom surface, and in which the upper body portion of said needle carrier member has a flat upper surface underlying and making flush abutment with said flat bottom surface, said mounting means mounting said needle carrier member on said syringe body portion for rotational movement about a central axis extending perpendicularly through the plane of its flat upper surface.

7. A multiple barrel syringe according to claim 6 in which said needle bore is offset from the central rotational axis of said needle carrier member.

8. A multiple barrel syringe according to claim 7 in which said mounting means includes an elongated journal member affixed to said syringe body portion and depending from the center of its bottom flat surface, and a recess centrally located in the flat upper surface of said needle carrier member and rotatably receiving said depending journal member.

9. A multiple barrel syringe according to claim 8 in which said elongated journal member includes a screw anchored in said syringe body portion and having an enlarged head, and in which said mounting means includes a compression spring interposed between said screw head and an overlying portion of said needle carrier member for urging the flat surfaces of said syringe body portion and said needle carrier member into firm flush abutment with each other.

10. A multiple barrel syringe according to claim 9 in which a resilient sealing member is mounted on the flat upper surface of said needle carrier member and positioned to underlie and seal off the outlet and of the fluid conduit which is out of communication with said needle bore when said needle carrier member is in either of its operative positions.

* * * * *